(12) United States Patent
Turner (10) Patent No.: US 9,790,939 B2
(45) Date of Patent: Oct. 17, 2017

(54) PERISTALTIC POSITIVE DISPLACEMENT PUMP APPARATUS

(71) Applicant: Tristel PLC, Snailwell Cambridgeshire (GB)

(72) Inventor: Jeremy Turner, Omorokoa (NZ)

(73) Assignee: Tristel PLC (GB)

( * ) Notice: Subject to any disclaimer, the term of this patent is extended or adjusted under 35 U.S.C. 154(b) by 45 days.

(21) Appl. No.: 14/432,644

(22) PCT Filed: Jul. 31, 2013

(86) PCT No.: PCT/GB2013/052047
§ 371 (c)(1),
(2) Date: Mar. 31, 2015

(87) PCT Pub. No.: WO2014/064415
PCT Pub. Date: May 1, 2014

(65) Prior Publication Data
US 2015/0233360 A1   Aug. 20, 2015

(30) Foreign Application Priority Data

Oct. 25, 2012 (GB) .................................... 1219218.3

(51) Int. Cl.
*F04B 53/06* (2006.01)
*F16K 15/14* (2006.01)
(Continued)

(52) U.S. Cl.
CPC .............. *F04B 53/06* (2013.01); *F04B 23/02* (2013.01); *F04B 43/12* (2013.01);
(Continued)

(58) Field of Classification Search
CPC ........... Y10T 137/7889; B05B 11/3032; B05B 11/3029; B05B 11/3033; F04B 23/02;
(Continued)

(56) References Cited

U.S. PATENT DOCUMENTS 424,944 A    4/1890  Allen
2,018,999 A  10/1935 De Bakey et al.
(Continued)

FOREIGN PATENT DOCUMENTS

EP    1914011 A2    4/2008
EP    1974825 A1   10/2008
(Continued)

*Primary Examiner* — Bryan Lettman
(74) *Attorney, Agent, or Firm* — Hayes Soloway PC (57) ABSTRACT

A pump apparatus (1) comprises a pump head (2) and a container (20) for a liquid to be dispensed. The pump head (2) has a flexible dispensing tube (4) in fluid connection with the inside of the container (20). The fluid connection between the dispensing tube (4) and the inside of the container (20) is provided by a supply tube (28) which co-operates with the dispensing tube (4) to provide a non-return valve function. An end (48) of the supply tube (28) is disposed within an end of the dispensing tube (4) and the non-return valve function is provided by a hole (46) through a side wall of the supply tube (28) in a region where the dispensing tube (4) overlaps the supply tube, whereby the dispensing tube (4) provides a seal over the hole (46) to prevent ingress of fluid when the internal pressure is lower than the external pressure. Another aspect of the invention provides a container (20) for use in the pump apparatus.

13 Claims, 14 Drawing Sheets

(51) Int. Cl.
  *F04B 43/12* (2006.01)
  *F04B 53/10* (2006.01)
  *F04B 23/02* (2006.01)
  *B05B 11/00* (2006.01)

(52) U.S. Cl.
  CPC ........ *F04B 53/1075* (2013.01); *F16K 15/142* (2013.01); *F16K 15/145* (2013.01); *B05B 11/30* (2013.01); *Y10T 137/7889* (2015.04)

(58) Field of Classification Search
  CPC ...... F04B 53/06; F04B 53/1075; F04B 43/12; F16K 15/142; F16K 15/145
  See application file for complete search history.

(56) References Cited

U.S. PATENT DOCUMENTS

| | | | | |
|---|---|---|---|---|
| 2,275,937 A * | 3/1942 | Baker | ............... | E21B 33/14 137/516.15 |
| 2,527,614 A | 10/1950 | Arpin | | |
| 3,674,024 A | 7/1972 | Cirillo | | |
| 3,786,683 A | 1/1974 | Berman et al. | | |
| 3,930,761 A * | 1/1976 | Barraclough | ........ | A61B 17/205 222/166 |
| 4,070,725 A * | 1/1978 | Austin | ................. | B05B 9/0426 222/192 |
| 4,159,790 A | 7/1979 | Bailey | | |
| 4,205,948 A | 6/1980 | Jones | | |
| 4,214,681 A | 7/1980 | Levine | | |
| 4,232,828 A | 11/1980 | Shelly, Jr. | | |
| 4,249,676 A | 2/1981 | Beery | | |
| 4,515,589 A | 5/1985 | Austin et al. | | |
| 4,722,731 A * | 2/1988 | Vailancourt | ............. | A61M 5/36 137/860 |
| 4,885,818 A | 12/1989 | Arterbury | | |
| 4,892,526 A * | 1/1990 | Reese | ................... | B05B 9/0426 604/290 |
| 5,755,263 A | 5/1998 | Jang | | |
| 6,293,762 B1 * | 9/2001 | Farkhan | ................ | B29C 73/166 417/234 |
| 6,505,986 B1 | 1/2003 | Oder | | |
| 2007/0119875 A1 | 5/2007 | Ehret et al. | | |
| 2008/0017670 A1 | 1/2008 | Tada | | |
| 2008/0118378 A1 * | 5/2008 | Baron | ................... | B67D 1/108 417/412 |
| 2009/0204132 A1 * | 8/2009 | Ortiz | ....................... | A61F 5/005 606/157 |
| 2010/0249717 A1 | 9/2010 | Salgia et al. | | |
| 2010/0313996 A1 * | 12/2010 | Breault | ................ | B05C 17/002 141/309 |
| 2012/0223161 A1 | 9/2012 | Goodwin et al. | | |

FOREIGN PATENT DOCUMENTS

| | | |
|---|---|---|
| GB | 1074594 | 7/1967 |
| WO | 9852863 A1 | 11/1998 |
| WO | 03011473 A1 | 2/2003 |
| WO | 2009105436 A1 | 8/2009 |

\* cited by examiner

PERISTALTIC POSITIVE DISPLACEMENT PUMP APPARATUS

BACKGROUND a. Field of the Invention

The present invention relates to a pump apparatus, notably to a peristaltic pump for use in sterile or clean-room environments, and to a container for use in the pump apparatus.

b. Related Art

A peristaltic pump is a positive displacement pump used to dispense a fluid from a container through a flexible dispensing tube. Hand-held peristaltic pumps are typically used to pump various fluids, such as a clean or sterile fluid, where there is a need for the pump not to contaminate the fluid, or to pump aggressive fluids such as adhesives, so that the fluid cannot contaminate the pump. A peristaltic pump allows delivery of a specified volume of fluid for a given actuation movement independently of the viscosity of the fluid.

U.S. 2010/0313996 describes a hand-held peristaltic pump apparatus for dispensing fluid from a rigid container. The apparatus includes a hand-operated peristaltic pump. The pump supports a rigid container which includes a fluid to be dispensed. A separate dispensing tube as well as a vent tube extends from the container through the pump.

The peristaltic pump is actuated by a user grasping the pump head in one hand, and using one or more fingers to depress a trigger which operates a rotary member that bears against the dispensing tube and the vent tube. Operation of the pump causes fluid to be pumped out from the container through the dispensing tube and air is pumped into the container through the vent tube so as to equalise pressure in the container.

A problem with the use of hand-held peristaltic pumps in sterile or clean-room environments is that not all of a user's fingers typically rest on the trigger. A user's finger which is not on the trigger is liable to trapped between the trigger and an adjacent surface of the pump head. This can cause damage to a glove worn by the user and contamination of the sterile or clean environment. Prolonged use may also promote repetitive strain injury (RSI).

Where it is necessary for the liquid in the container to be sterilised by irradiation by gamma or other rays, this causes heating of the liquid up to about 55° C. and creates an internal pressure. Such pressure is not released by a vent tube which passes through the pump head because, like the dispensing tube, the vent tube is sealed by pressure of the peristaltic rotary member. In this case, the vent tube may instead be open to atmosphere via a one-way valve such as a duck-bill valve, although such a vent/valve arrangement does not allow air to be pumped into the container to replace liquid which is pumped out. Use of a collapsible container instead of a rigid container allows the internal pressure to be adjusted by reduction in the internal volume of the container as liquid is pumped out. However, it is desirable to reduce the complexity of the pump.

SUMMARY OF THE INVENTION

Aspects of the invention are specified in the independent claims. Preferred features are specified in the dependent claims.

The invention provides a pump apparatus and a container for a pump apparatus with simplified construction.

BRIEF DESCRIPTION OF THE DRAWINGS

The invention will now be further described, by way of example only, with reference to the following drawings, in which.

DETAILED DESCRIPTION

Figure 1:
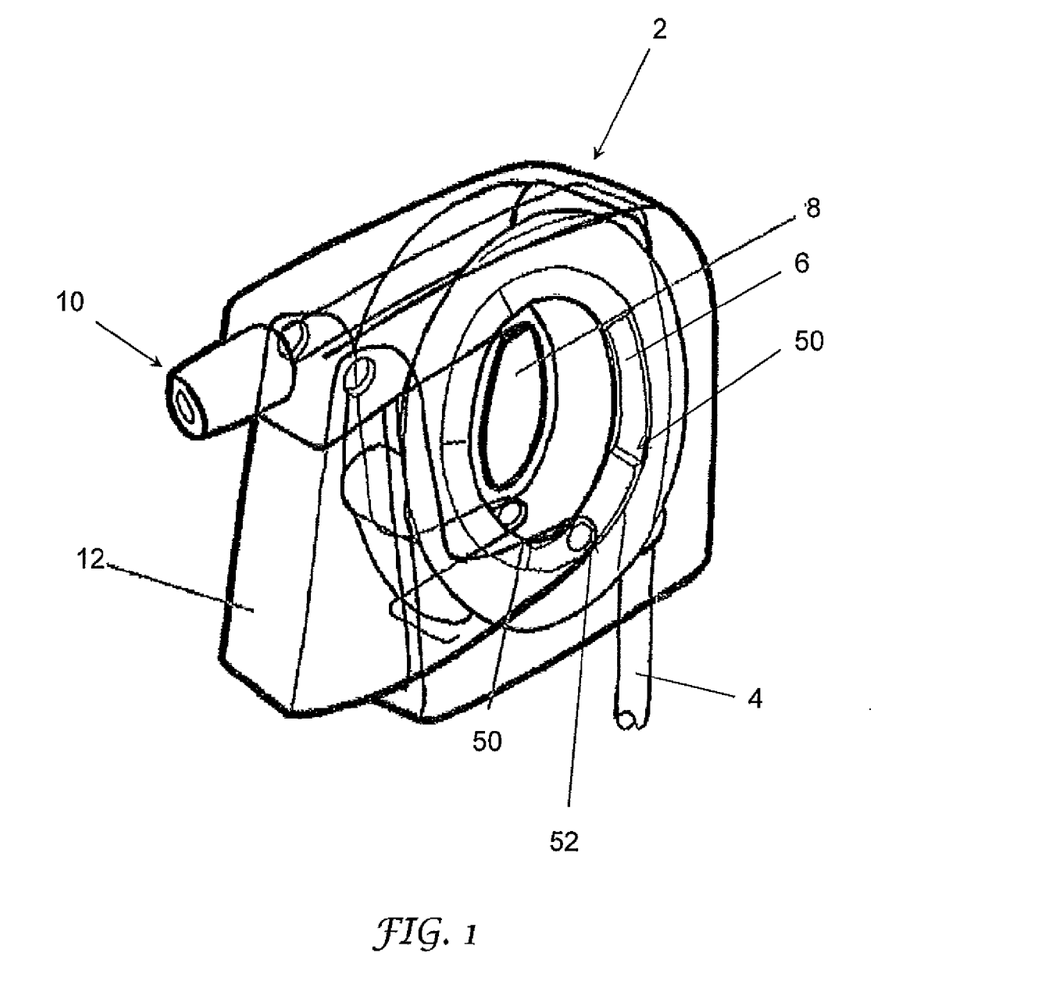
FIG. 1 shows a pump head for use in a hand-held peristaltic pump apparatus in accordance with an embodiment of the invention.

Referring to FIG. 1, a pump head 2 houses a rotatable peristaltic pump member 6 and a flexible dispensing tube 4 disposed through the pump head 2. The pump head 2 includes a finger-actuated trigger 12 which is provided with at least one pawl member 52. Actuation of the trigger 12 causes turning of the pump member 6 in one direction only, by interaction between the pawl member 52 and ratchet features 50 on the pump member 6. At least one impeller 36 (best shown in FIG. 4) acts on the dispensing tube 4 to squeeze the tube 4 against an inner surface of the pump head. As the pump member 6 turns, the impeller 36 drives fluid ahead of it through the dispensing tube and out through a nozzle 10.

The volume squeezed out by the impeller 36 is independent of the viscosity of the fluid within the dispensing tube 4 The dispensing tube 4 is elastomeric, at least in the region where the impeller 36 acts upon it, to ensure that the tube returns to its original cross-sectional shape when not acted upon by an impeller. In a preferred embodiment, the dispensing tube 4 is elastomeric along its entire length. In this embodiment, the dispensing tube 4 is of a unitary construction and formed from a silicone rubber.

Figure 2:
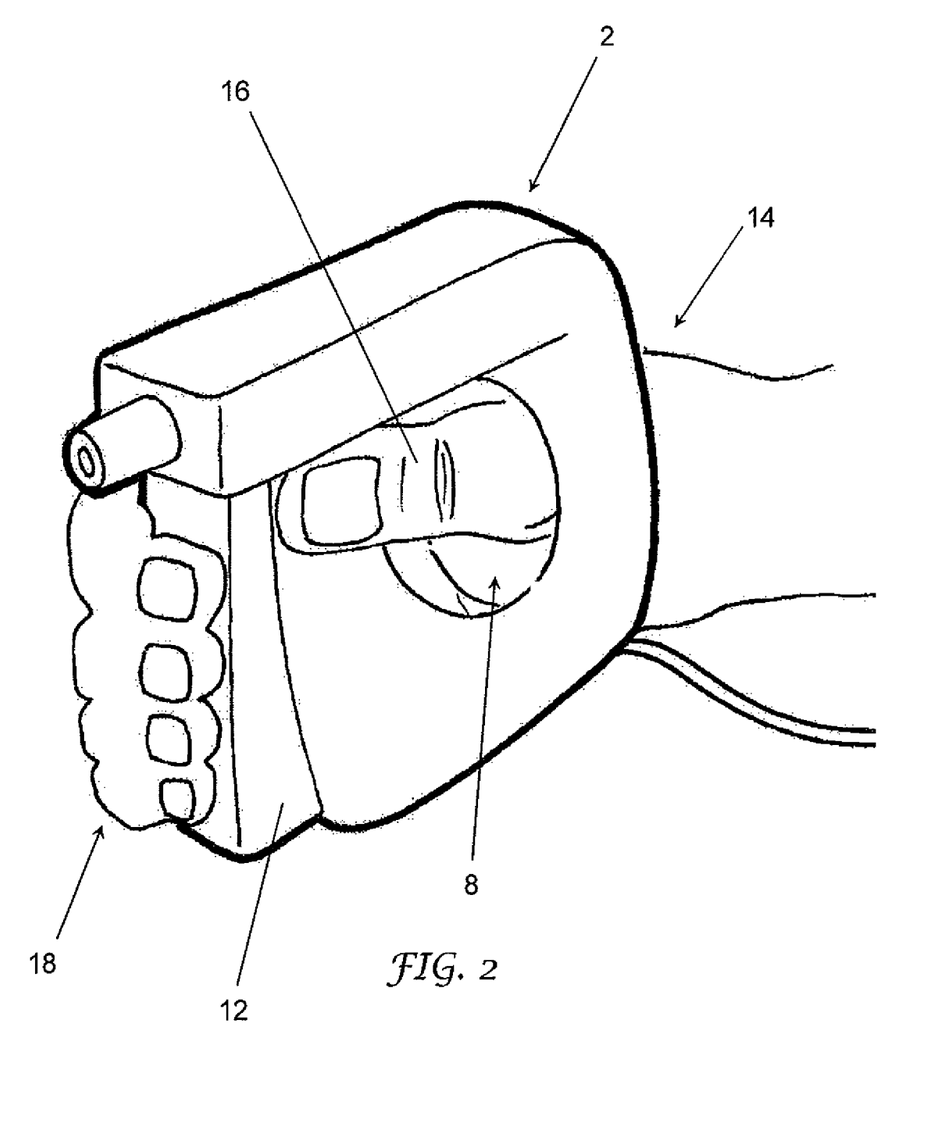
FIG. 2 illustrates the pump head of FIG. 1 in use.
Figure 4:
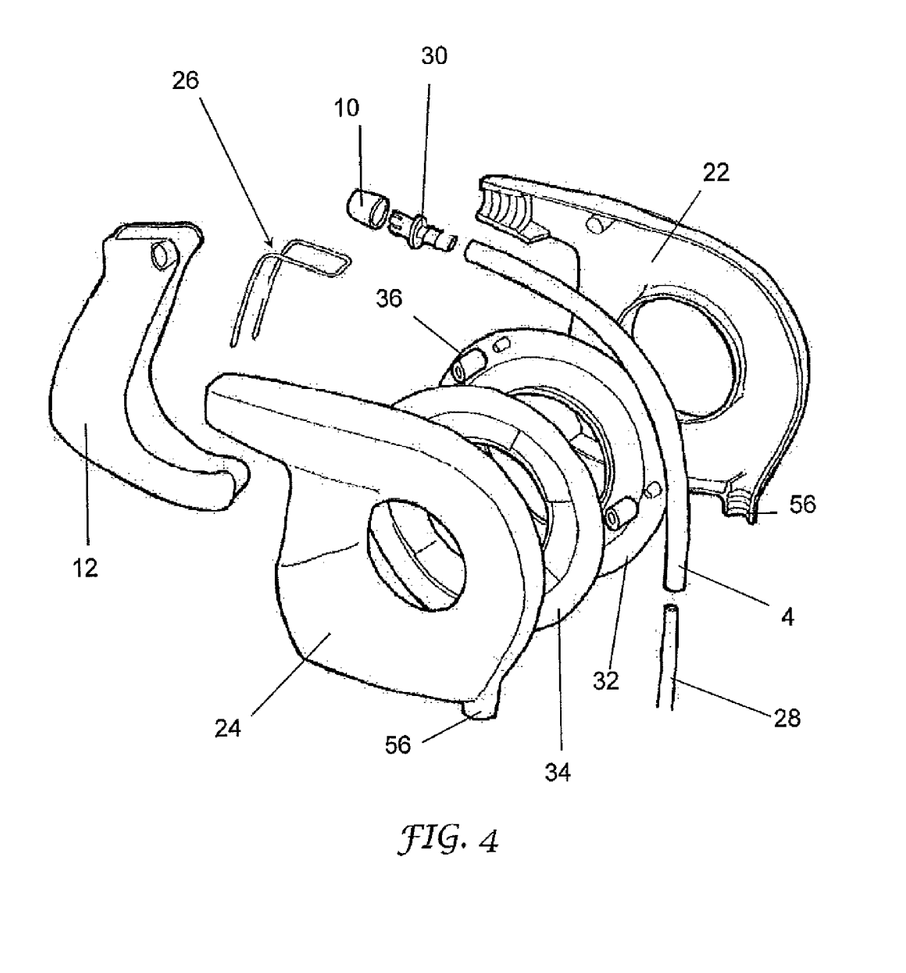
FIG. 4 is an exploded view of the pump head of FIG. 1.

The pump head 2 is provided with a thumb hole 8 disposed within an area around which the peristaltic pump member 6 turns when actuated. This arrangement permits a user's hand 14 to grip the pump head 2 by locating the thumb 16 in the thumb hole 8 and all the user's fingers 18 on the trigger 12. This has the benefit that no part of a user's finger will be trapped between the trigger 12 and the housing (22,24) of the pump head 2 (FIG. 4). Such trapping can cause tearing of a user's glove and contamination of a sterile or clean-room environment in which the pump head is being used, as well as potential finger damage. The arrangement allows the pump head to be of sufficient size to accommodate a rotary peristaltic pump member of a large enough diameter not to cause kinking or flattening of the dispensing tube as a result of its conforming to the curvature of the pump member. Location of all fingers on the trigger 12 is also ergonomic and helps reduce RSI from repeated trigger actuation compared to a conventional trigger sprayer in which not all fingers act on the trigger. In this example, the thumb hole has a central axis which is substantially coincident with an axis of rotation of the peristaltic pump member 6.

Figure 3:
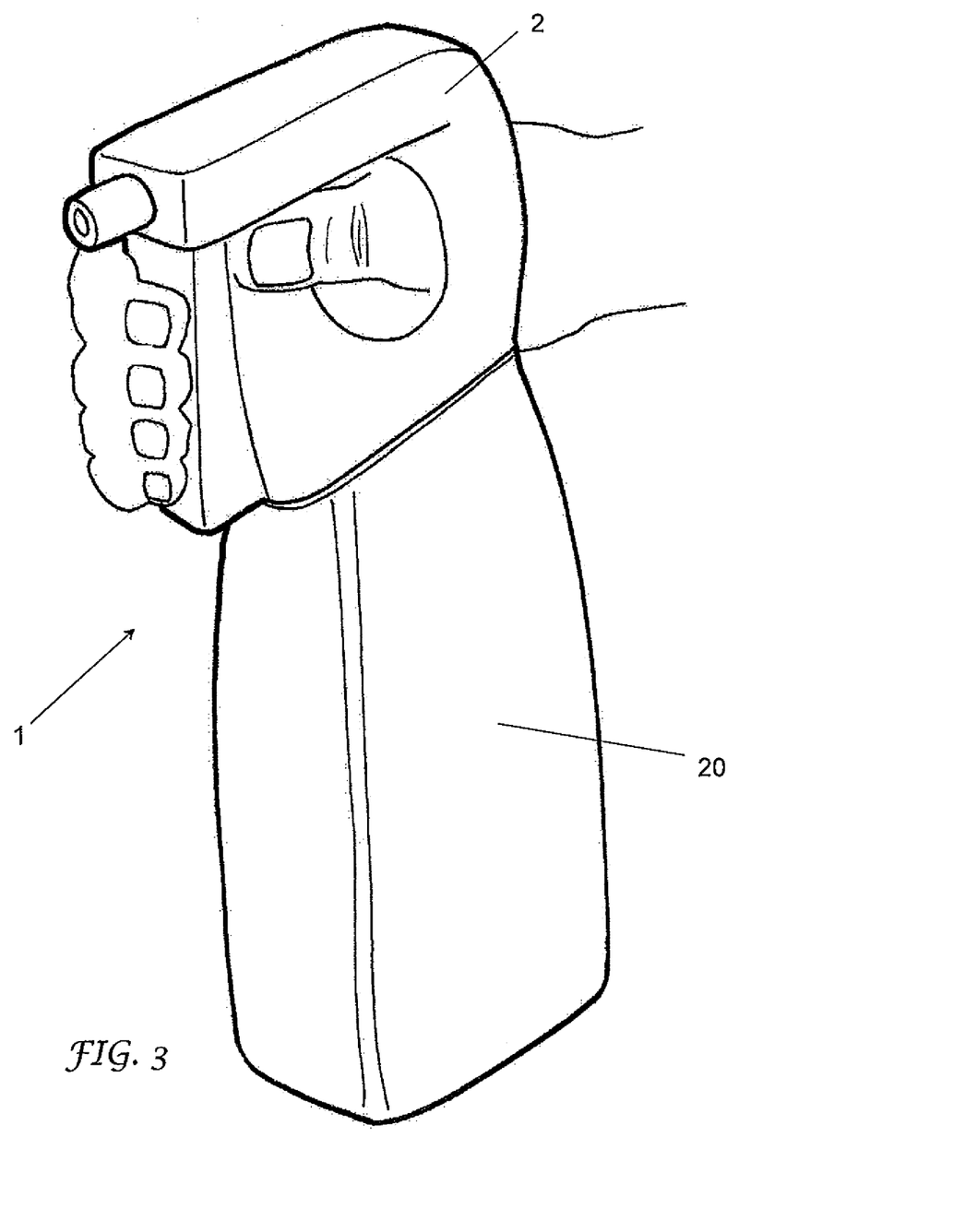
FIG. 3 shows an embodiment of a hand-held peristaltic pump apparatus in accordance with an embodiment of the invention.

An embodiment of a hand-held peristaltic pump apparatus 1 shown in FIG. 3 includes a rigid container 20 attached to the pump head 2 and containing a liquid to be dispensed. The dispensing tube 4 is in fluid connection with the liquid and will be dispensed through the nozzle 10 when the user squeezes the trigger.

Referring now to FIG. 4, the exemplified pump head 2 is assembled from opposed parts 22,24 which co-operate to define a pump housing to which the trigger 12 is pivotally mounted and biased by a return spring 26. The peristaltic pump member is formed from opposed drive wheels 32,34 connected together by impellers 36 and rotatably mounted within the pump housing. The dispensing tube 4 is disposed around the pump member and connected at one end to the nozzle 10 via a connector 30 and at the other end to a supply tube 28 as will be further described in more detail presently. The dispensing tube 4 fits securely around the connector 30, which co-operates with the nozzle 10 to provide a nozzle assembly. Sealing of the nozzle assembly in the pump head is achieved by means of the dispensing tube 4, which is preferably formed of a silicone rubber. Sealing of the nozzle assembly in the pump head is also achieved by means of the dispensing tube 4. In this example the final seal is ultrasonically welded once the supply tube 28 has been connected. It will be appreciated that other methods may be used to achieve the final seal; suitable methods will be known to those skilled in the art.

Figure 5:
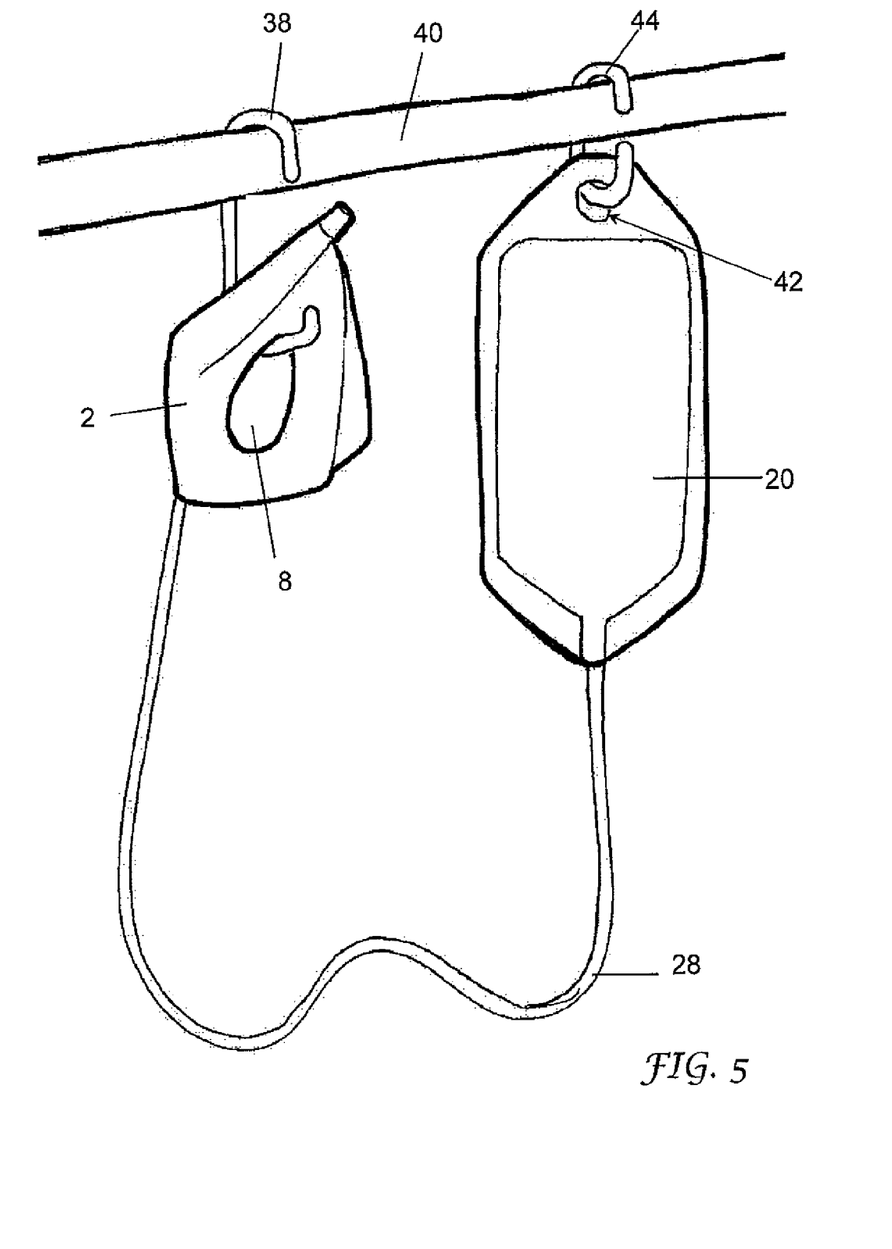
FIG. 5 shows another embodiment of a pump apparatus in accordance with the invention, in a storage configuration.

The container 20 need not be rigidly connected to the pump head 2. Indeed, it is preferred that the container 20 is connected to the pump head 2 only by the dispensing tube 4 and optionally via the supply tube 28. This allows the container to be supported by means other than the user holding it and relieves the user from carrying the weight of the container. Referring to FIG. 5, the container 20 is a collapsible bag and is provided with a feature 42 to enable it to be hung from a bar or other support structure 40. The exemplified feature 42 is a hole through which a hook 44 passes. The pump head 2 may also be hung up when not in use, for example by means of a hook 38 through the thumb hole 8.

Figure 6:
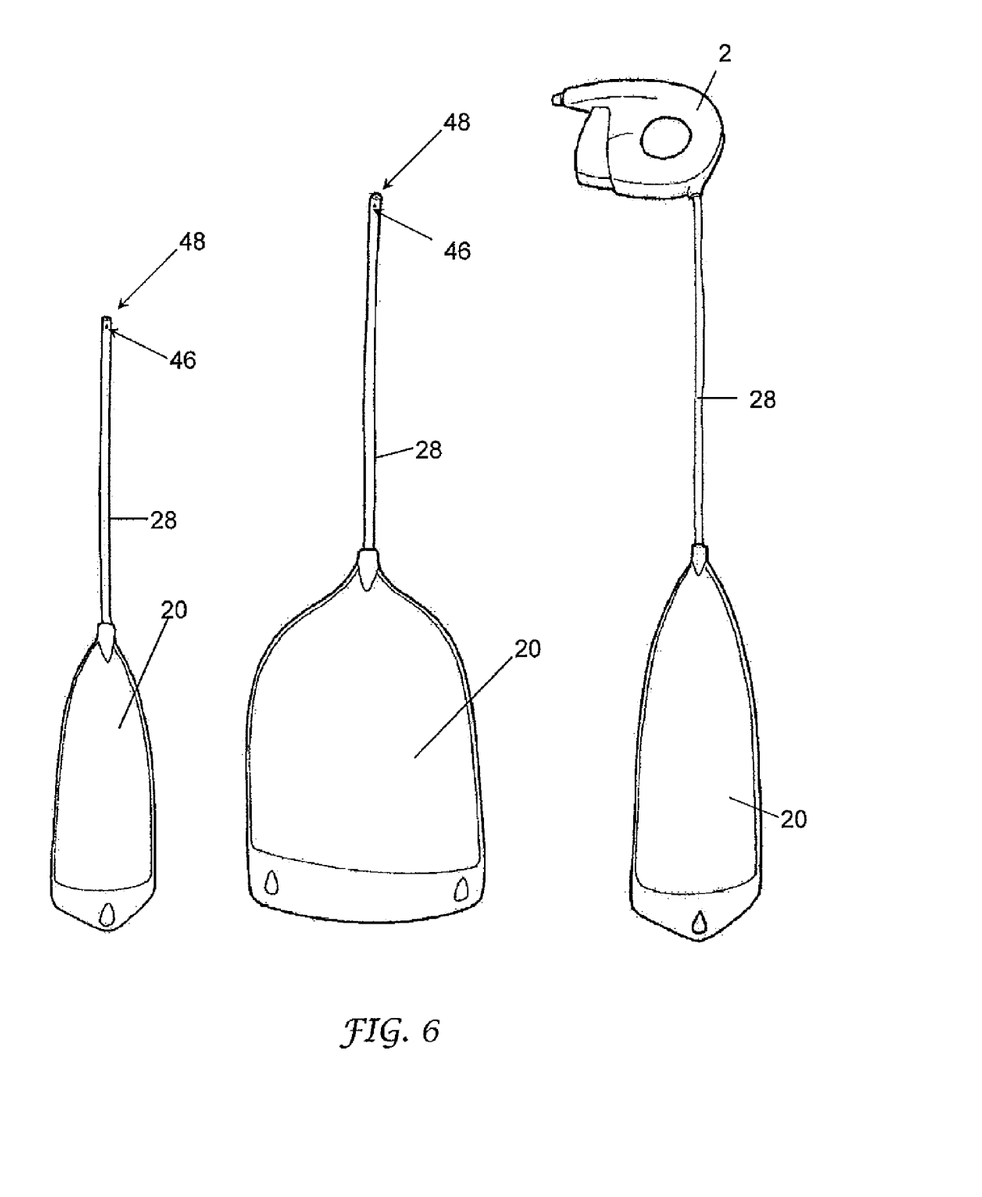
FIG. 6 shows the pump apparatus of FIG. 5 in use, and alternative embodiments of container for use in the pump apparatus.

When the pump apparatus is in use the tubing 28 connecting the container 20 to the pump head 2 allows the user to carry out fluid pumping operations some distance from the container, which may be supported in various ways. Referring to FIG. 6, the tubing 28 is shown fully extended and may have may have any desired length, for example a length in the range 1-3 meters, preferably about 1.5 m. Containers 20 of different capacity may be used, as illustrated in the left hand and centre representations of FIG. 6 which have, respectively, 1 liter and 3 liter capacities. The proximal end of the supply tube 28 is located inside the container 20 and in fluid contact with liquid therein. Adjacent to the distal end 48 of the supply tube 28, the wall of the supply tube has a hole 46 extending all the way through the wall.

Figure 7:
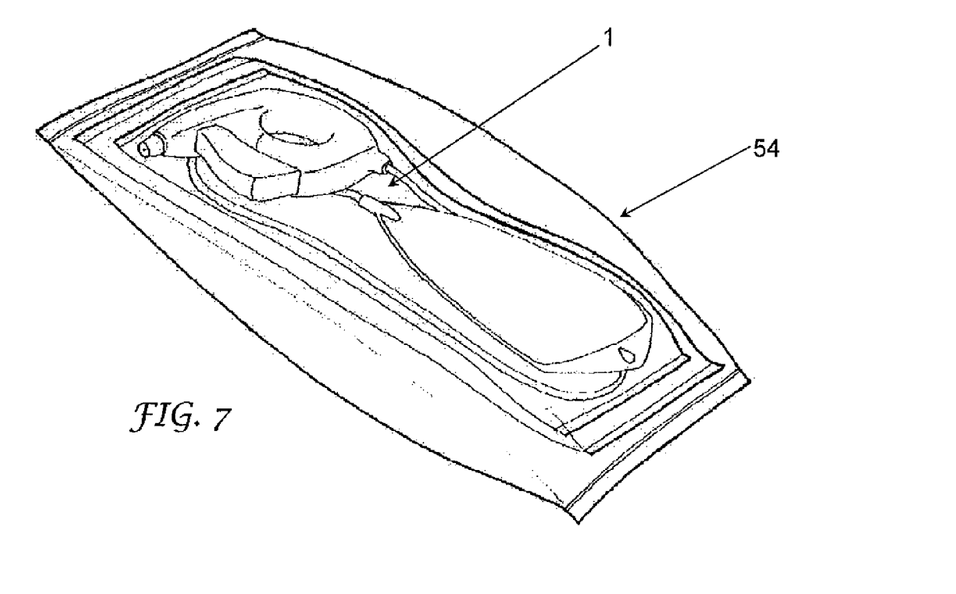
FIG. 7 illustrates the pump apparatus of FIG. 5 in a sterile, packaged condition.
Figure 8:
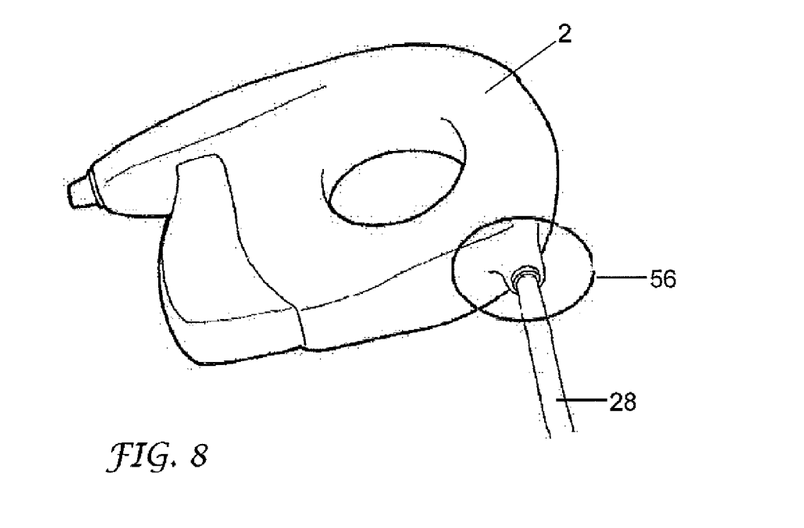
FIG. 8 shows the valve location in an embodiment of the pump apparatus.

When the pump apparatus 1 is to be used in a sterile environment, it is triple-bagged 54 and gamma-irradiated to kill any pathogens. The process of gamma-irradiation causes liquid in the container 20 to heat up substantially, for example to about 55° C., which creates an internal pressure. To release this pressure, a non-return valve is required, and in this example is provided in the overlap of the supply tube 28 and the dispensing tube 4 inside the pump head 2 by an interference detail 56 indicated in FIG. 8.

Figure 9:
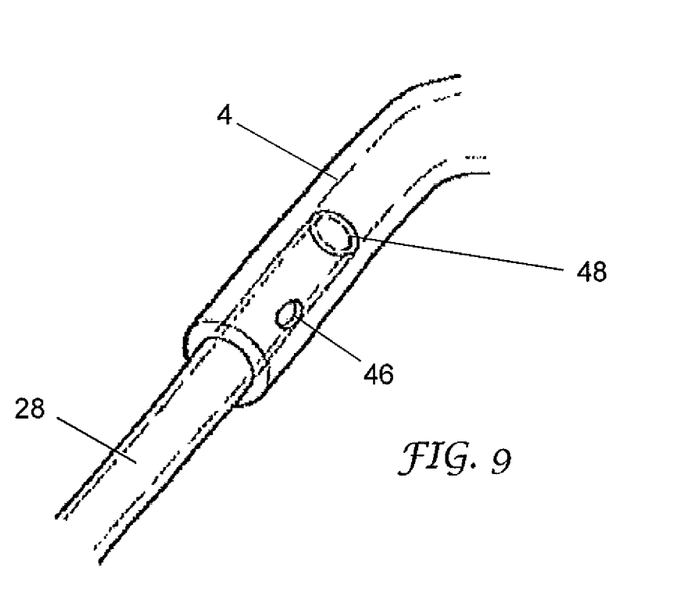
FIGS. 9-11 illustrate the non-return valve arrangement of pump apparatus in accordance with an embodiment of the invention.
Figure 10:
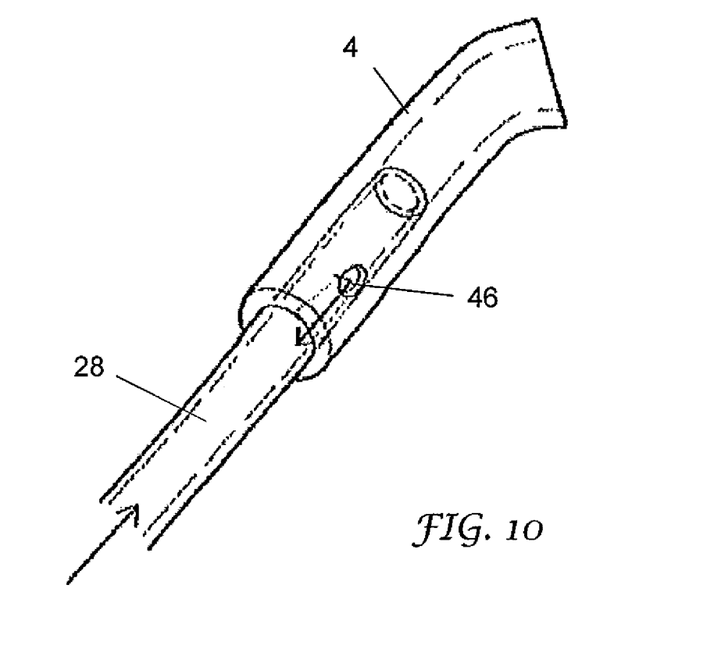
Figure 11:
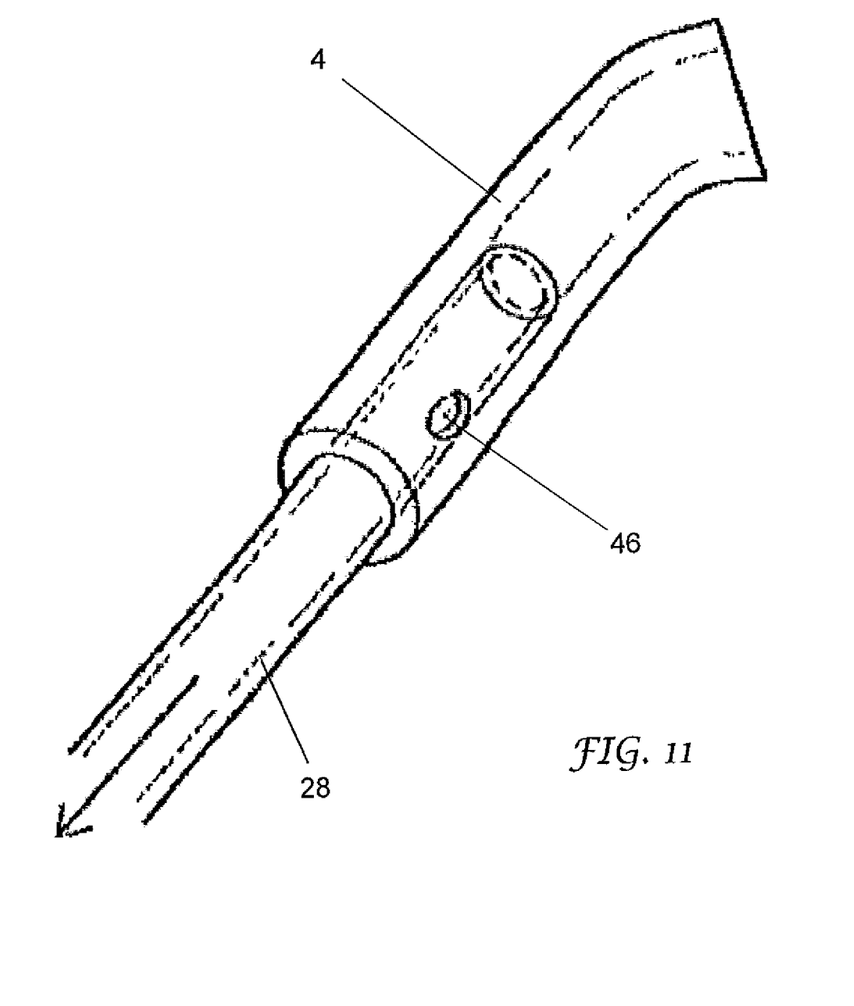

Referring now to FIGS. 9-11, the non-return valve arrangement formed by connection of the dispensing tube 4 and supply tube 28 is shown. In this example the supply tube is made of PVC and the dispensing tube is made of a silicone rubber. The distal end 48 of the supply tube 28 is disposed within and is a close fit for the dispensing tube 4. The hole 46 is also within the dispensing tube 4. The interference detail 56 clamps the dispensing tube 4 to the supply tube 28 within the pump head 2, but the hole 46 is not clamped so is free to release. When pressure is applied from the supply tube 28 (FIG. 10) from the liquid container 20 the dispensing tube stretches away from the hole 46 allowing gas to flow out and relieve the pressure. When the liquid in the container cools down and the pressure is reversed (FIG. 11) the rubber wall of the dispensing tube is sucked over the hole 46 and creates a seal. Thus, the dispensing tube provides a seal over the hole to prevent ingress of fluid when the internal pressure in the container is lower than the external (atmospheric) pressure.

This arrangement avoids the need for a separate vent tube and provides a pump apparatus of simplified construction.

Figure 12:
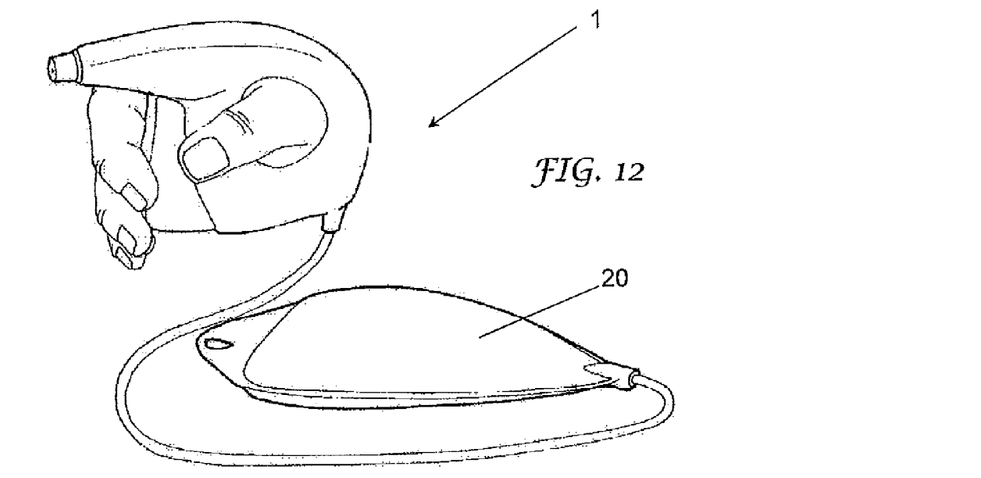
FIGS. 12-14 illustrate further embodiments of a pump apparatus in accordance with the invention.
Figure 13:
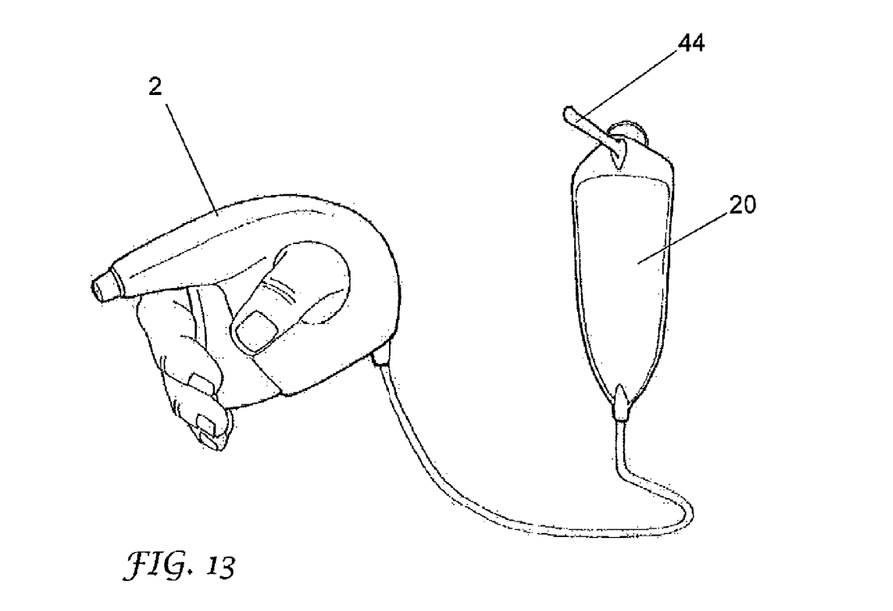
Figure 14:
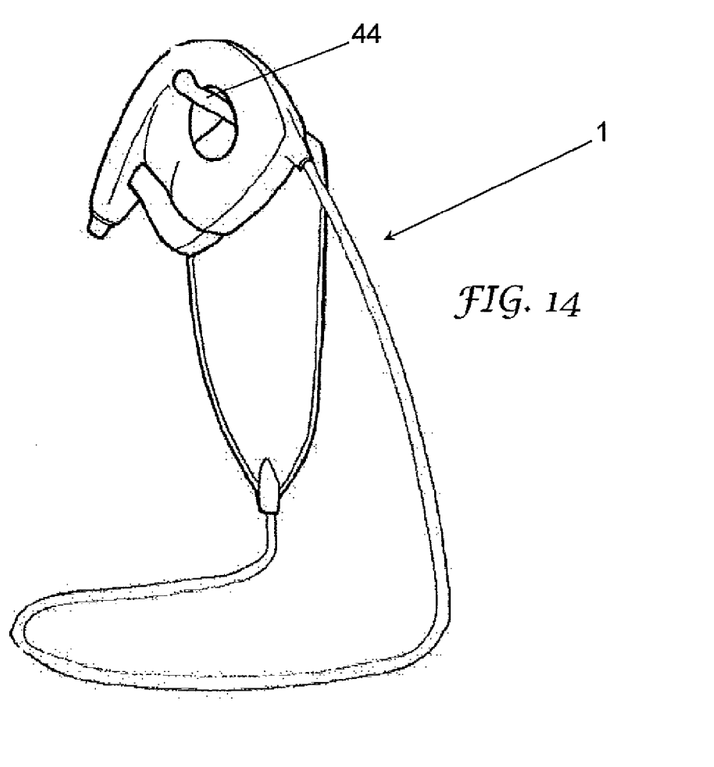
Figure 15:
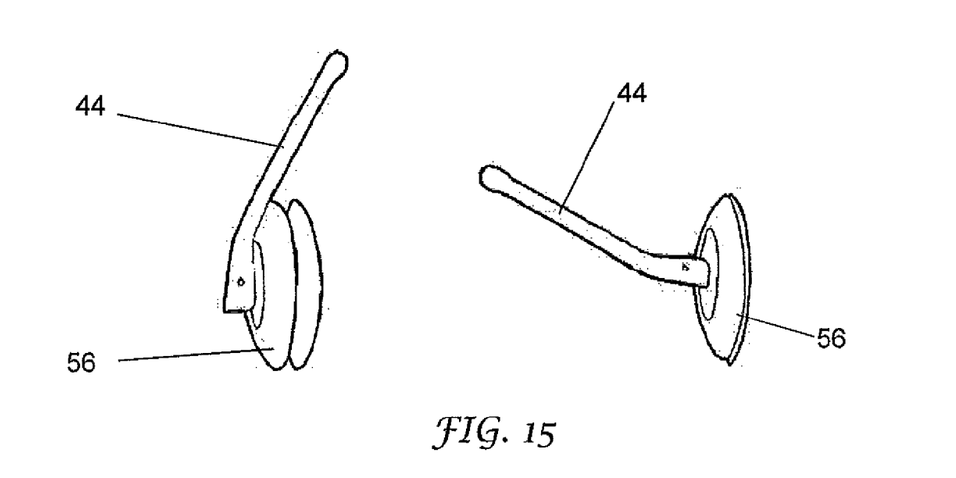
FIG. 15 shows hooks for use with the embodiments of FIGS. 12-14.

The container 20 may be placed on the ground (FIG. 12) while in use, or hung from a hook 44 (FIG. 13) from which the pump head 2 may also be hung when not in use (FIG. 14). The hook 44 may be provided with a suction cup 56 for attachment to any suitable smooth surface; the hook 44 may be pivotable between an attaching position and an attached position, shown in the left and right representations respectively of FIG. 15.

Figure 16:
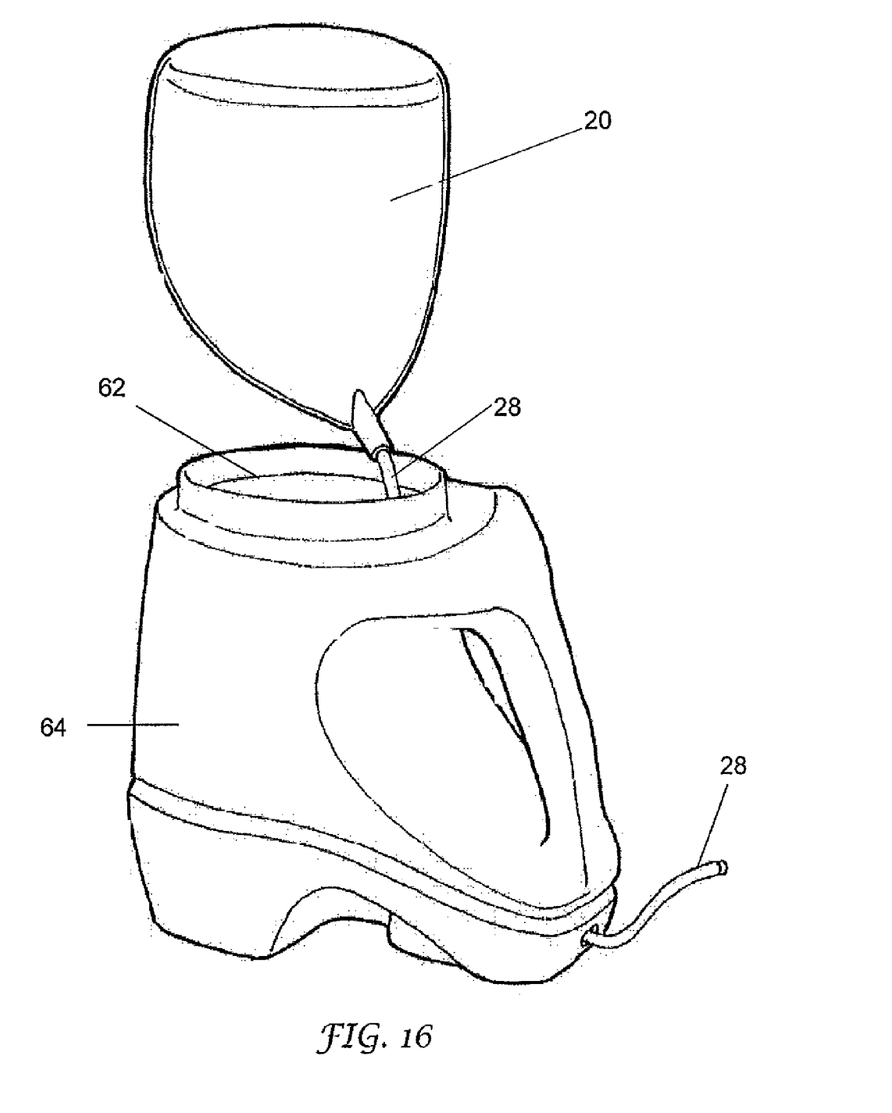
FIGS. 16-18 show pump apparatus in accordance with a further embodiment of the invention.
Figure 17:
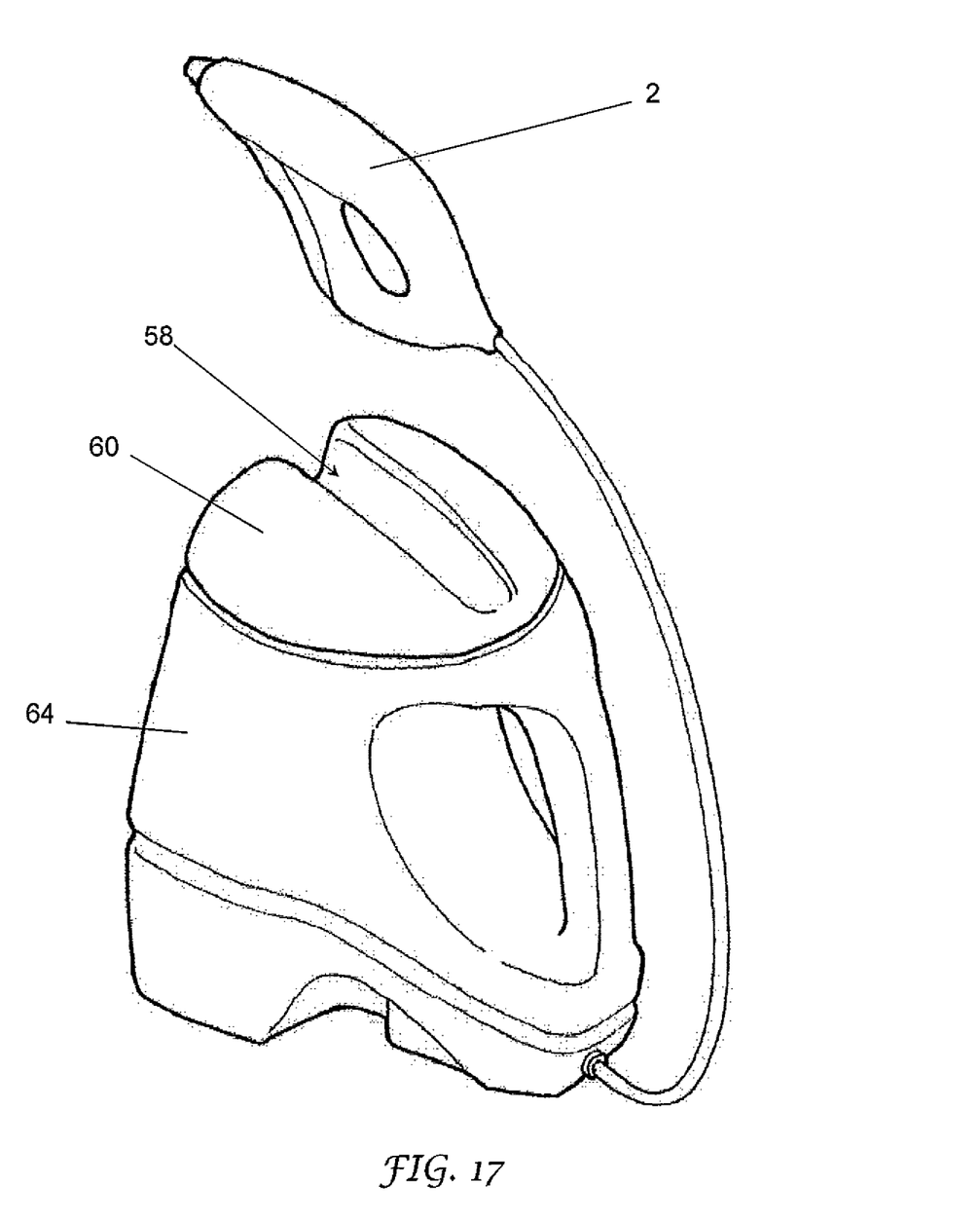
Figure 18:
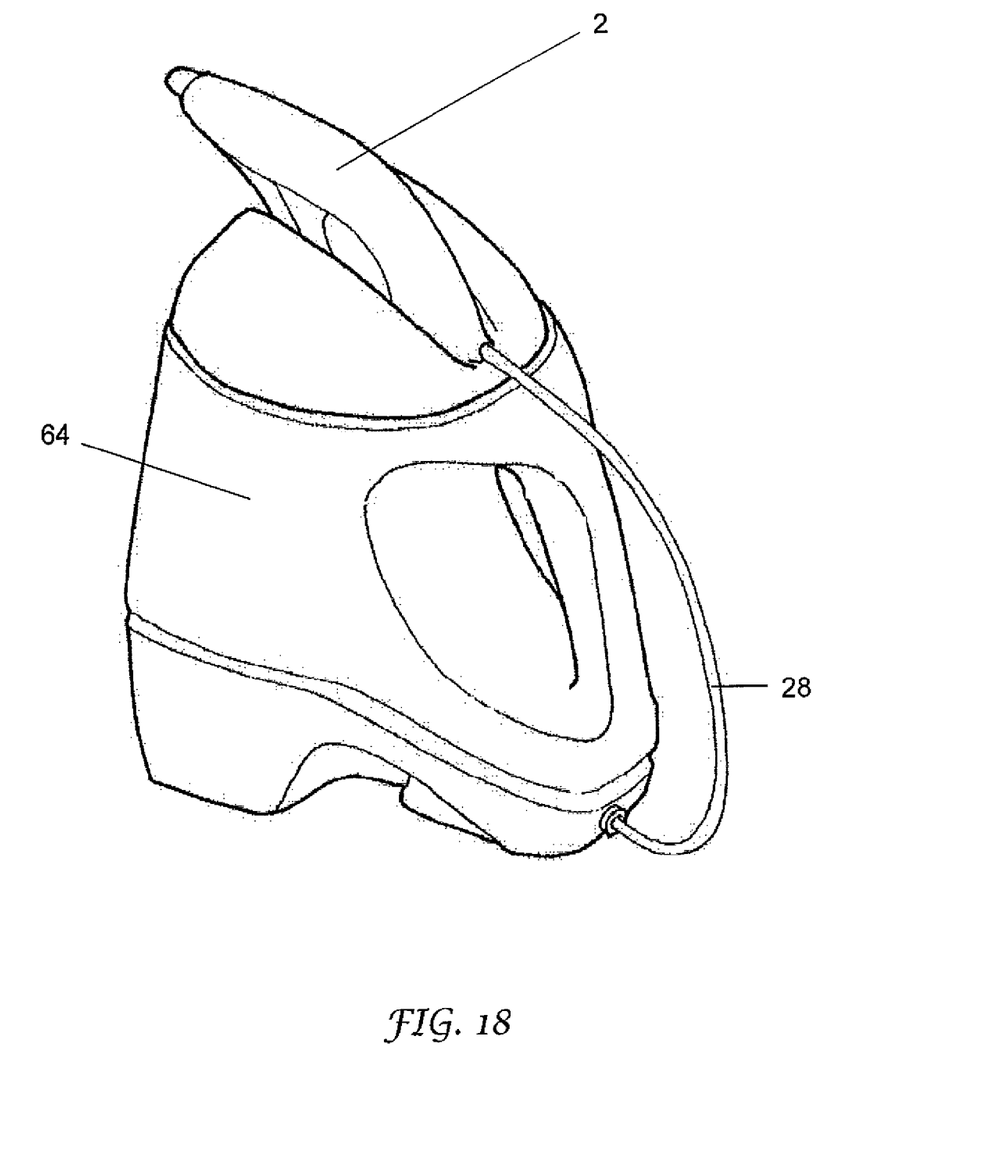

In the embodiment shown in FIGS. 16-18 the container 20 is collapsible and is housed in a substantially rigid container housing 64, in this example a flagon. The container 20 is placed in the flagon through an opening 62 and the supply tube 28 in this example is disposed through a hole at the base of the flagon. The flagon 64 has a moulded feature 58 which provides a seat for the pump head 2 when not in use. In this example the feature 58 is provided in a cap 60 which covers the opening 62.

It is envisaged that the pump head 2 and container housing 64 will be reused, and the container 20 is a refill component which will be replaced as needed.

It will be understood that the container 20 and supply tube 28 may be manufactured and sold independently of the pump head. Accordingly, another aspect of the invention provides a container specified. Although the invention has been illustrated with respect to a hand-held peristaltic pump head of a particular design, it will be understood that the invention is not limited to this embodiment and the pump head may take any conventional form, notably one in which the dispensing tube is sealed when not in use.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable combination.

What is claimed is:

1. A pump apparatus comprising a pump head and a container for a liquid to be dispensed;
    the pump head having a flexible dispensing tube in a fluid connection with an inside of the container;
    the fluid connection between the dispensing tube and the inside of the container being provided by a supply tube which directly connects to the dispensing tube, wherein the supply tube connected to the dispensing tube also provides a non-return valve function in a relief flow path, which communicates the inside of the dispensing tube and the supply tube to a space external to the tubes;
    wherein an open end of the supply tube is disposed within an end of the dispensing tube to provide the fluid connection and wherein the non-return valve function is provided by a hole through a side wall of the supply tube in a region where the dispensing tube overlaps the supply tube, whereby the dispensing tube provides a seal over the hole to prevent an ingress of fluid into the dispensing tube and the supply tube from the space external to the dispensing tube and the supply tube when an internal pressure in the dispensing tube and the supply tube in the region is lower than an external pressure on the dispensing tube and the supply tube in the region and wherein the dispensing tube allows for an egress of fluid from the dispensing tube and the supply tube through the hole in the sidewall and between the dispensing tube and the supply tube to the space external to the dispensing tube and the supply tube when the internal pressure is higher than the external pressure on the dispensing tube and the supply tube in the region.

2. The pump apparatus according to claim 1, wherein the dispensing tube is formed of silicone rubber.

3. The pump apparatus according to claim 1, wherein the container is connected to the pump head only by the supply tube.

4. The pump apparatus according to claim 1, wherein the container is connected to the pump head only by at least one of the supply tube and the dispensing tube.

5. The pump apparatus according to claim 1, wherein a length of the flexible dispensing tube which connects the pump head to the container is in a range of 1-3 meters.

6. The pump apparatus according to claim 1, wherein the container is adapted to be hung from a support structure.

7. The pump apparatus according to claim 1, wherein the container is collapsible and is housed in a rigid container housing.

8. The pump apparatus according to claim 7, wherein the container housing is provided with a seat for receiving the pump head when the pump head is not in use.

9. The pump apparatus according to claim 1, wherein the pump head is a peristaltic pump head.

10. The pump apparatus according to claim 1, the pump head having a nozzle; wherein sealing of the nozzle is provided by an engagement between the dispensing tube and the nozzle.

11. A method of sterilizing the pump apparatus according to claim 1, having the liquid in the container, the method comprising irradiating the pump apparatus with gamma radiation and permitting a gas pressure, generated by a heating of the liquid caused by the irradiating, to be reduced by an escape of gases through the non-return valve function.

12. The container for the liquid to be dispensed by the pump apparatus as specified in claim 1, the container including the supply tube, wherein the supply tube has a free end and the hole in the side wall is adjacent the free end.

13. A peristaltic pump apparatus comprising a pump head and a container for a liquid to be dispensed;
    the pump head having a peristaltic pump member and a flexible dispensing tube in a fluid connection with an inside of the container;
    the fluid connection between the dispensing tube and the inside of the container being provided by a supply tube which directly connects to the dispensing tube, wherein the supply tube connected to the dispensing tube also provides a non-return valve function in a relief flow path, which communicates the inside of the dispensing tube and the supply tube to a space external to the tubes;
    wherein an open end of the supply tube is disposed within an end of the dispensing tube to provide the fluid connection and wherein the non-return valve function is provided by a hole through a side wall of the supply tube in a region where the dispensing tube overlaps the supply tube upstream of the peristaltic pump member, whereby the dispensing tube provides a seal over the hole to prevent an ingress of fluid into the dispensing tube and the supply tube from the space external to the dispensing tube and the supply tube when an internal pressure in the dispensing tube and the supply tube in the region is lower than an external pressure on the dispensing tube and the supply tube in the region and wherein the dispensing tube allows for an egress of fluid from the dispensing tube and the supply tube through the hole in the sidewall and between the dispensing tube and the supply tube to the space external to the dispensing tube and the supply tube when the internal pressure is higher than the external pressure on the dispensing tube and the supply tube in the region.

* * * * *